United States Patent [19]

Asakura et al.

[11] Patent Number: 4,804,454

[45] Date of Patent: Feb. 14, 1989

[54] OXYGEN CONCENTRATION SENSING APPARATUS

[75] Inventors: Masahiko Asakura; Yasunari Seki; Takanori Shiina; Minoru Muroya, all of Wako, Japan

[73] Assignee: Honda Giken Kagyo Kabushiki Kaisha, Tokyo, Japan

[21] Appl. No.: 28,138

[22] Filed: Mar. 19, 1987

[30] Foreign Application Priority Data

Mar. 19, 1986 [JP] Japan .................................. 61-63203

[51] Int. Cl.⁴ ............................................ G01N 27/58
[52] U.S. Cl. .................................. 204/406; 204/412; 204/425; 204/426
[58] Field of Search ................ 204/1 T, 406, 410–412, 204/425–426

[56] References Cited

U.S. PATENT DOCUMENTS

| | | | |
|---|---|---|---|
| 4,440,621 | 4/1984 | Kitahara | 204/406 |
| 4,578,171 | 3/1986 | Yamada et al. | 204/406 |
| 4,586,476 | 5/1986 | Asayama | 123/440 |
| 4,594,139 | 6/1986 | Asayama et al. | 204/410 |
| 4,601,809 | 7/1986 | Kitahara | 204/406 |
| 4,609,452 | 9/1986 | Shimomura | 204/425 |
| 4,622,125 | 11/1986 | Ogama et al. | 204/425 |
| 4,622,126 | 11/1986 | Shimomura | 204/425 |
| 4,702,816 | 10/1987 | Hashimoto | 204/421 |

FOREIGN PATENT DOCUMENTS 8103410  3/1982  United Kingdom .

Primary Examiner—John F. Niebling
Assistant Examiner—Ben C. Hsing
Attorney, Agent, or Firm—Birch, Stewart, Kolasch & Birch

[57] ABSTRACT

An oxygen concentration sensing apparatus includes an oxygen pump element and a sensor cell element to be placed in a gas under measurement, and a device for generating a voltage value command indicating a voltage to be generated across electrodes of the sensor cell element. A current limit device is provided so that the supply of the voltage value command is stopped to decrease a pump current to the oxygen pump element gradually when the voltage generated across the electrodes of the sensor cell element exceeds a first predetermined voltage, and the pump current to the oxygen pump element is reduced immediately when the voltage generated across the electrodes of the sensor cell element exceeds a second predetermined voltage which is higher than the first predetermined voltage.

4 Claims, 2 Drawing Sheets

OXYGEN CONCENTRATION SENSING APPARATUS

BACKGROUND OF THE INVENTION

1. Field of the Invention

The present invention relates to an oxygen concentration sensing apparatus, and more particularly to an oxygen concentration sensing apparatus for sensing the oxygen concentration in a gas such as an engine exhaust gas.

2. Description of Background Information

In order to accelerate the purification of the exhaust gas and to improve the fuel economy of an internal combustion engine, a feedback type air/fuel ratio control system is used, in which oxygen concentration in the exhaust gas is detected and air/fuel ratio of the mixture supplied to the engine is controlled to a target air/fuel ratio by a feedback control operation in accordance with a result of the detection of the oxygen concentration.

As an oxygen concentration sensor for use in such an air/fuel ratio control system, there is a type which is capable of producing an output signal whose level is proportional to the oxygen concentration in the exhaust gas of the engine, and the detail of which is disclosed in Japanese Patent Application No. 61,63203, laid open No. 58-153155. This oxygen concentration sensor includes an oxygen concentration sensing unit having a general construction including a pair of flat solid electrolyte members having oxygen ion permeability. These oxygen ion conductive solid electrolyte members are placed in the gas under measurement, and electrodes are respectively provided on the front and back surfaces of both of the solid electrolyte members. In other words, each pair of electrodes sandwich each solid electrolyte member. These two solid electrolyte members each having a pair of electrodes are arranged in parallel so as to face each other and forming a gap portion therebetween, or in other words, a restricted region between them.

With this arrangement, one of the solid electrolyte members serves as an oxygen pump element and the other one of the solid electrolyte members serves as a sensor cell element for sensing an oxygen concentration ratio. In an ambient atmosphere of the gas under measurement, a drive current is supplied across the electrodes of the oxygen pump element in such a manner that the electrode facing the gap portion operates as a negative electrode. By the supply of this current, i.e. a pump current, the oxygen component of the gas in the gap portion is ionized on the surface of the negative electrode of the oxygen pump element. The oxygen ions migrate through the inside of the oxygen pump element to the positive electrode, where the oxygen ions are released from the surface thereof in the form of the oxygen gas.

While this movement of the oxygen ions is taking place, the oxygen concentration becomes different for the gas in the gap portion and the gas outside the sensor cell element because of a decrease of the oxygen gas component in the gap portion. Therefore, a voltage develops across the electrodes of the sensor cell element. If the magnitude of the pump current supplied to the oxygen pump element is controlled so that the voltage generated across the sensor cell element is maintained constant, the magnitude of the pump current varies substantially in proportion to the oxygen concentration in the exhaust gas under a condition of a constant temperature. The pump current is then used as an output signal indicative of the oxygen concentration detection value.

In this type of oxygen concentration sensor, if an excessive current is supplied to the oxygen pump element, it causes the blackening phenomenon by which the oxygen ions are removed from the solid electrolyte members. For instance, when zirconium dioxide ($ZrO_2$) is used as the solid electrolyte, the oxygen ions $O_2$ are taken from the zirconium dioxide ($ZrO_2$) and zirconium (Zr) is separated out. As a result of this blackening phenomenon, the deterioration of the oxygen pump element takes place rapidly, to cause a debasement of the operation of the oxygen concentration sensor as a whole. Therefore, the pump current value must be controlled to be lower than values in a region of generation of the blackening phenomenon (blackening phenomenon generation region) so as to prevent the blackening phenomenon before it is generated.

FIG. 1 shows lines indicating the pump current to the oxygen pump element versus oxygen concentration relation and a boundary line of the generation of the blackening phenomenon with respect to different values of the voltage Vs developing at the sensor cell element, which voltage functions as a parameter. As illustrated, magnitude of the current $I_P$ varies in proportion to the oxygen concentration, and the rate of variation is different for several different values of the voltage $V_s$. In other words, the voltage Vs is a parameter which determines the relation between the magnitude of the current $I_P$ and the oxygen concentration. As illustrated in this figure, the boundary line of the generation of the blackening phenomenon is shown, like the relation between the pump current and the oxygen concentration, as a first-degree function of the oxygen concentration value. Therefore, whether or not the pump current value belongs to values in the blackening phenomenon generation region can be determined from the value of the voltage Vs. Therefore, if the voltage Vs exceeds a predetermined voltage, it can be considered that the value of the pump current is approaching the region of the generation of the blackening phenomenon, and the generation of the blackening phenomenon can be prevented by reducing the pump current. However, if the magnitude of the pump current is controlled in such a way, the pump current will ee reduced even if the voltage Vs exceeds the predetermined voltage only for an instant. In such a case, a problem arises that the magnitude of the pump current fluctuates after the voltage Vs is reduced to be lower than the predetermined voltage, and the oxygen concentration will not be detected accurately.

OBJECT AND SUMMARY OF THE INVENTION

An object of the present invention is to provide an oxygen concentration sensing apparatus of an oxygen concentration proportional current detection type, by which the generation of the blackening phenomenon is surely prevented and the oxygen concentration is detected accurately.

According to the present invention, an oxygen concentration sensing apparatus comprises:

an oxygen sensing unit being sensitive to oxygen in a gas under measurement and operative to produce an output signal having a magnitude proportional to the concentration of oxygen in the gas under measurement when contacted by a stream of the gas and having a sensor cell element made of a first active plate of an oxygen ion conductive solid electrolyte and a first pair of electrodes sandwiching the active plate, an oxygen pump element made of a second active plate of an oxygen-ion conductive solid electrolyte and a second pair of electrodes sandwiching the active plate, the first and second active plates confronting a restricted region into which the gas under measurement is introduced;

command generating means for generating a voltage value command representing a voltage to be generated across the first pair of electrodes of the sensor cell element;

delay means for delaying the voltage value command from the command generating means;

current supply means for supplying a pump current across the second pair of electrodes of the oxygen pump element so that a voltage generated across the electrodes of the sensor cell element equals the voltage represented by the voltage value command, in which a current value of the pump current to the oxygen pump element is output as the output signal indicating the measured oxygen concentration; and limit means for stopping the supply of an excess current to the electrodes of the oxygen pump element by the current supply means, the limit means including first switch means for stopping the supply of the voltage value command from the command generating means to the delay means when the voltage generated across tee electrodes of the sensor cell element exceeds a first predetermined voltage, and second switch means for immediately reducing the pump current across the electrodes of the oxygen pump element when the voltage generated across the electrodes of the sensor cell element exceeds a second predetermined voltage which is higher than the first predetermined voltage.

DETAILED DESCRIPTION OF THE PREFERRED EMBODIMENT

An embodiment of the present invention will be explained with reference to the accompanying drawing.

Figure 1:
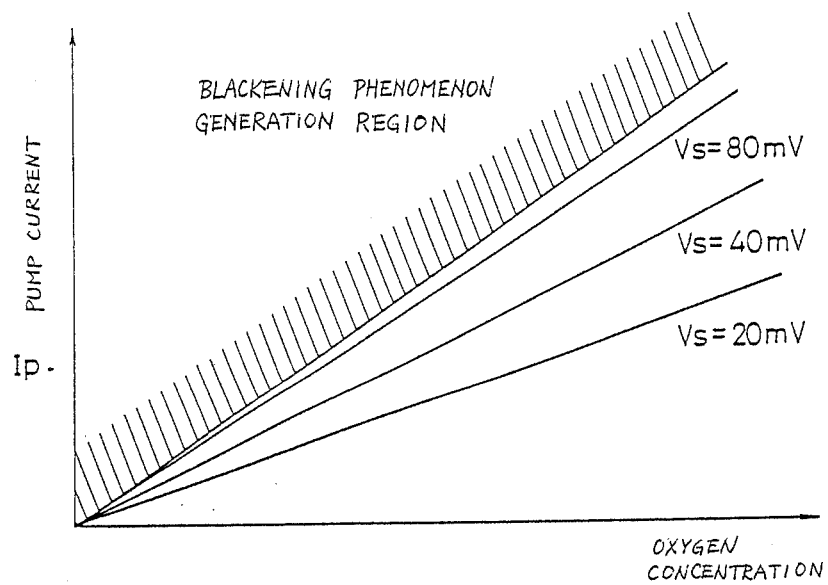
FIG. 1 is a diagram illustrating lines representing oxygen concentration versus pump current characteristics and a boundary of generation of the blackening phenomenon.
Figure 2:
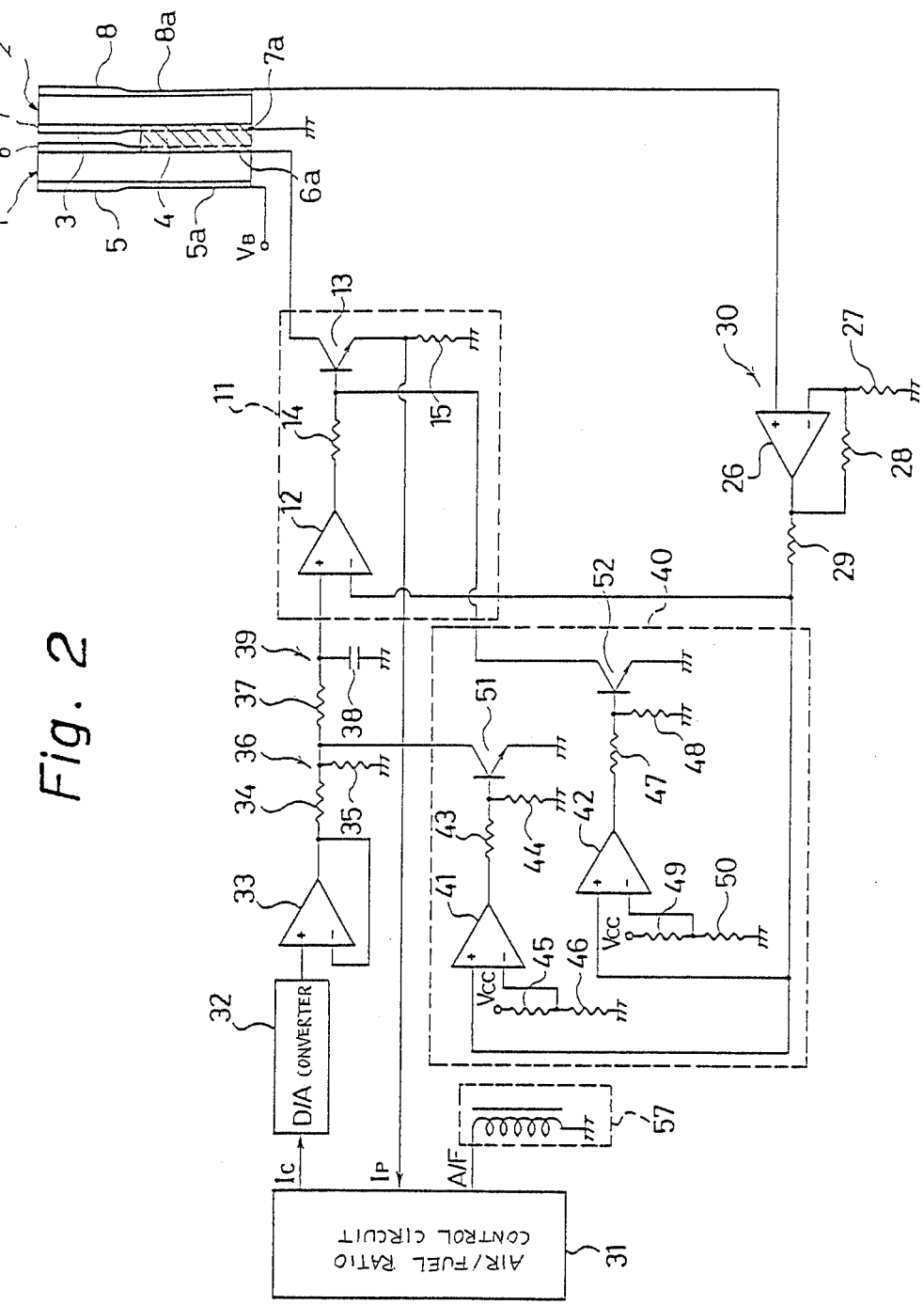
FIG. 2 is a circuit diagram of an embodiment of the oxygen concentration sensing apparatus according to the present invention.

FIG. 2 shows an example of air/fuel ratio control system in which the oxygen concentration sensing apparatus according to the present invention is utilized. In this system, the oxygen concentration sensing device which is made up of a pair of flat active elements, namely an oxygen pump element 1 and a sensor cell element 2 arranged in parallel to each other, is mounted in an exhaust pipe (not shown) of an internal combustion engine. The main portions of the oxygen pump element 1 and the sensor cell element 2 are made of an oxygen-ion conductive solid electrolyte member. An end portion of the oxygen pump element 1 and an end portion of the sensor cell element 2 which face each other are spaced apart so as to form a gap portion (or a restricted region) 3 between them. The other end portions of the oxygen pump element 1 and the sensor cell element 2 are connected to each other by means of a spacer 4. The oxygen pump element 1 and the sensor cell element 2 are provided with, at their free end portions and on both sides thereof, square electrodes 5 through 8 which are made of a porous heat-proof metal. Further, lead wires 5a through 8a of the square electrodes 5 through 8 respectively, are provided on both surfaces of the connected end portions of the oxygen pump element 1 and the sensor cell element 2. The square electrodes 6 and 7 are located in the inner sides of the oxygen pump element 1 and the sensor cell element 2 facing the gap portion 3. Therefore, they are also referred to as inner electrodes. Similarly, the square electrodes 5 and 8 located in the outer sides of the oxygen pump element 1 and the sensor cell element 2 are also referred to as outer electrodes.

Across the electrodes 5 and 6 of the oxygen pump element 1, a current (pump current) is supplied from a current source 11. The current source 11 is made up of an operational amplifier 12, an NPN transistor 13, and resistors 14 and 15. More particularly, an output terminal of the operational amplifier 12 is connected to the base of the transistor 13 via the resistor 14. The emitter of the transistor 13 is connected to the ground via the resistor 15. The resistor 15 is provided in order to detect the magnitude of the pump current $I_P$ flowing between the electrodes 5 and 6 of the oxygen pump element 1. A voltage across the terminals of the resistor 15 is supplied to an $I_P$ input terminal of an air/fuel ratio control circuit 31 as a signal indicative of the magnitude of the pump current. The collector of the transistor 13 is connected to the inner electrode 6 of the oxygen pump element 1 through the lead wire 6a. The outer electrode 5 of the oxygen pump element 1 is supplied with a voltage $V_B$ through the lead wire 5a.

On the other hand, the inner electrode 7 of the sensor cell element 2 is grounded through the lead wire 7a, and the outer electrode 8 of the sensor cell element 2 is connected, through the lead wire 8a, to a non-inverting amplifier 30 which is made up of an operational amplifier 26 and resistors 27 through 29. An output terminal of the non-inverting amplifier 30 is connected to an inverting input terminal of the operational amplifier 12. An $I_c$ control output terminal of the air/fuel ratio control circuit 31 is connected to a D/A converter 32 which, in turn, generates a voltage corresponding to a digital data provided at the Ic control output terminal of the air/fuel ratio control circuit 31. The output terminal of the D/A converter 32 is connected to the non-inverting input terminal of the operational amplifier 12 through a voltage follower circuit 33 made up of an operational amplifier, a voltage dividing circuit 36 of resistors 34 and 35, and an integration circuit 39 made up of a resistor 37 and a capacitor 38.

A limiter circuit 40 is connected to an output terminal of the non-inverting amplifier 30. The limiter circuit 40 is made up of operational amplifiers 41 and 42, resistors 43 through 50, and NPN transistors 51 and 52. The operational amplifiers 41 and 42 respectively operate as a comparator. The operational amplifier 41 compares an output voltage of the non-inverting amplifier 30 with a voltage divided signal of a voltage Vcc obtained by the resistors 45 and 46. An output terminal of the operational amplifier 41 is connected to the base of the transistor 51 through a voltage dividing circuit made up of the resistors 43 and 44. The emitter of the transistor 51 is grounded and its collector is connected to a connection line between the voltage dividing circuit 36 and the integration circuit 39. On the other hand, the operational amplifier 42 compares the output voltage of the non-inverting amplifier 30 with a voltage divided signal of the voltage Vcc obtained by the resistors 49 and 50. An output terminal of the operational amplifier 42 is connected to the base of the transistor 52 through a voltage dividing circuit made up of the resistors 47 and 48. The emitter of the transistor 52 is grounded and its collector is connected to the base of the transistor 13. With these circuit elements, the operational amplifier 41, the resistors 43 thrugh 46 and the transistor 51 form first switch means, and the operational amplifier 42, the resistors 47 through 50, and the transistor 52 form second switch means.

The air/fuel ratio control circuit 31 has an A/F drive terminal in addition to the above mentioned Ic output terminal and $I_P$ input terminal. A solenoid valve 57 for controlling the supply of the secondary air is connected to the A/F drive terminal. The solenoid valve 57 is provided in an air intake side secondary air supply passage which connects to an intake air passage of the engine, at a position downstream of the throttle valve of a carburetor.

With this circuit construction, when the digital signal is supplied from the Ic control terminal of the air/fuel ratio control circuit 31 to the D/A converter 32 as a voltage value command representing a voltage to be generated across the electrodes 7 and 8 of the sensor cell element, the digital signal is converted to a voltage at the D/A converter 32, and this converted voltage is in turn supplied to the voltage dividing circuit 36 through the voltage follower circuit 33. The voltage dividing circuit 36 divides the output voltage of the voltage follower circuit 33 at a voltage dividing ratio which is determined by the resistance of the resistors 34 and 35, and supplies a voltage divided output to the integration circuit 39. An output voltage of the integration circuit 39 gradually increases in accordance with an integration time constant determined by the resistor 37 and the capacitor 38, and becomes stable when it reaches the output voltage of the voltage dividing circuit 36. This output voltage of the integration circuit 39 is supplied to the non-inverting input terminal of the operational amplifier 12 as a reference voltage Vr1. Upon starting of the supply of this reference voltage Vr1, the voltage level at the inverting input terminal of the operational amplifier 12 is lower than the reference voltage Vr1. Therefore, the output signal level of the operational amplifier 12 is at a high level, and the transistor 13 turns on. Due to the on state of the transistor 13, the pump current flows across the electrodes 5 and 6 of the oxygen pump element 1.

By the flow of the pump current, a voltage Vs appears across the electrodes 7 and 8 of the sensor cell element 2. The voltage Vs is supplied to the non-inverting amplifier 30 in which this voltage Vs is amplified, and the amplified voltage is in turn supplied to the inverting input terminal of the operational amplifier 12. When the voltage Vs rises, an output voltage Vs' of the non-inverting amplifier 30 also goes up. If the voltage Vs' becomes higher than the reference voltage Vr1, the output level of the operational amplifier 12 turns low, to turn off the transistor 13. Due to the off state of the transistor 13, the pump current decreases to reduce the voltage Vs appearing across the electrodes 7 and 8 of the sensor cell element 2. As a result, the voltage Vs' from the non-inverting amplifier 30 supplied to the inverting input terminal of the operational amplifier 12 decreases. When the voltage Vs' becomes lower than the reference voltage Vr1, the output signal of the operational amplifier 12 turns to the high level, to increase the pump current. Since these operations are repeated at a high speed, the voltage Vs is controlled to a constant value, and it becomes equal to a voltage corresponding to a value indicated by digital signal.

The magnitude of the pump current $I_P$ flowing through the electrodes 5 and 6 of the oxygen pump element 1 when the reference voltage Vr1 is supplied to the operational amplifier 12, is detected by means of a terminal voltage of the resistor 15, and this terminal voltage is supplied to the $I_P$ input terminal of the air/fuel ratio control circuit 31. Then, the air/fuel ratio control circuit 31 detects whether or not the pump current value $I_P$ is smaller than a reference value Ir corresponding to a target air/fuel ratio. If $I_P < Ir$, it is determined that the air/fuel ratio of the mixture supplied to the engine is rich, and the solenoid valve 57 is driven in an opening direction, so that the secondary air is supplied to the engine. If $I_P \geq Ir$, it is determined that the air/fuel ratio of the mixture supplied to the engine is lean, and the drive of the solenoid valve 57 in the opening direction is stopped, so that the supply of the secondary air is stopped.

Further, when the voltage Vs across the electrodes 7 and 8 of the sensor cell element 2 rises, the output voltage Vs' of the non-inverting amplifier 30 rises as well. When the voltage Vs exceeds a first predetermined voltage (60 mV, for instance) the voltage Vs' exceeds the voltage divided signal obtained by the resistors 45 and 46, and the output voltage of the operational amplifier 41 turns from a low level to the high level. By this high level output voltage of the operational amplifier 41, the transistor 51 turns on, so that the voltage at the connecting line between the voltage dividing circuit 36 and the integration circuit 39 is made equal to the ground level. Therefore, electric charge which has been accumulated in the capacitor 38 flows in the form of an electric current to the ground through the resistor 37 and the transistor 51. Thus, the terminal voltage of the capacitor 38, that is, the reference voltage Vr1 reduces gradually. By the above mentioned operation of the current supply circuit 11, the pump current supplied to the oxygen pump element 1 reduces gradually. In this way, if the output voltage Vs' of the non-inverting amplifier 30 reaches a voltage level near the blackening phenomenon generation region, the pump current decreases gradually.

If the pump current has further increased to a level within the blackening phenomenon generation region, the voltage Vs exceeds a second predetermined voltage (80 mV, for example). As a result, the output voltage Vs' of the non-inverting amplifier 30 exceeds the voltage divided signal obtained by the resistors 49 and 50, and the output signal level of the operational amplifier 42 turns from the low level to the high level. By this high level output signal of the operational amplifier 42, the transistor 52 turns on, so that the electric potential at the base of the transistor 13 equals the ground level. Therefore, the transistor 13 turns off, to decrease the pump current. By this operation, the pump current is decreased rapidly if it has risen to a level within the blackening phenomenon generation region.

In addition, an integration circuit made up of a resistor and a capacitor is used in the above described embodiment. However, this is not limitative, and the integration circuit could utilize, for example, a resistor and an inductor can as well.

In the oxygen concentration sensing apparatus of the type detecting a current value proportional to the oxygen concentration according to the present invention, the voltage value command representing a voltage to be generated at the sensor cell element is delayed by the delay means. The pump current is supplied in accordance with this delayed voltage value command, and the supply of the voltage value command is stopped when the voltage generated across the electrodes of the sensor cell element exceeds a first predetermined voltage. Therefore, the pump current is gradually decreased when the voltage generated across the electrodes of the sensor cell element exceeds the first predetermined voltage. Therefore the generation of the blackening phenomenon, which causes a rapid degradation of the elements of the oxygen concentration sensor, can be prevented. Moreover, when the voltage generated across the electrodes of the sensor cell element rises to a level near the blackening phenomenon generation region only for an instant, a rapid reduction of the pump current is avoided and the fluctuation of the pump current prevented. Therefore, the accuracy of the detection of the oxygen concentration can be improved as compared with conventional arrangements. Further, when the voltage generated across the electrodes of the sensor cell element has reached a level above the second predetermined voltage which is higher than the first predetermined voltage, the amount of the current supplied to the electrodes of the oxygen pump element is decreased rapidly, so that it becomes possible to cope with a rapid increase of the pump current into the blackening phenomenon generation region. Thus, the generation of the blackening phenomenon is surely prevented by the oxygen concentration sensing apparatus according to the present invention.

What is claimed is:

1. An oxygen concentration sensing apparatus comprising:
   oxygen sensing means, responsive to oxygen in a gas under measurement, for producing an output signal having a magnitude proportional to the concentration of oxygen in the gas under measurement when contacted by a stream of the gas, said oxygen sensing means having,
      a sensor cell element made of a first active plate of an oxygen ion conductive solid electrolyte and a first pair of electrodes sandwiching said first active plate,
      an oxygen pump element made of a second active plate of an oxygen-ion conductive solid electrolyte and a second pair of electrodes sandwiching said second active plate,
      said first and second active plates defining a restricted region into which said gas under measurement is introduced;
   command generating means for generating a voltage value command representing a voltage to be generated across said first pair of electrodes of said sensor cell element;
   delay means for gradually supplying said voltage value command supplied by said command generating means;
   current supply means, responsive to said gradually supplied voltage value command received from said delay means, for supplying a pump current across said second pair of electrodes of said oxygen pump element so that a voltage generated across said electrodes of said sensor cell element equals said voltage represented by said voltage value command, said current supply means further developing a current value of said pump current supplied to said oxygen pump element as said output signal indicating the measured oxygen concentration; and
   limit means for stopping the supply of an excess current to said electrodes of said oxygen pump element by said current supply means, said limit means including,
      first switch means for stopping the supply of said voltage value command from said command generating means to said delay means when said voltage generated across said electrodes of said sensor cell element exceeds a first predetermined voltage, and
      second switch means for immediately reducing said pump current across said electrodes of said oxygen pump element when said voltage generated across said electrodes of said sensor cell element exceeds a second predetermined voltage which is higher than said first predetermined voltage.

2. An oxygen concentration sensing apparatus as set forth in claim 1, wherein said delay means comprises a charge-discharge circuit whose output signal level increases gradually when the voltage value command is supplied from said command generation means, and decreases gradually when said supply of said voltage value command is stopped by said first switch means.

3. The oxygen concentration sensing apparatus of claim 2 wherein said first switch means gradually reduces said pump current by stopping the supply of said voltage value command to said delay means.

4. The oxygen concentration sensing apparatus of claim 1 wherein said gas under measurement is the exhaust of an internal combustion engine.

* * * * *